(12) United States Patent
Majumder et al.

(10) Patent No.: US 6,613,737 B1
(45) Date of Patent: *Sep. 2, 2003

(54) PROCESS FOR THE PURIFICATION OF A NEW MOTILITY-PROMOTING PROTEIN FROM BUFFALO SERUM: A SLAUGHTER HOUSE WASTE

(75) Inventors: Gopal Chandra Majumder, Calcutta (IN); Mahitosh Mandal, Calcutta (IN); Saswati Banerjee, Calcutta (IN)

(73) Assignee: Council of Scientific and Industrial Research, New Delhi (IN)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 805 days.

(21) Appl. No.: 09/037,409

(22) Filed: Mar. 10, 1998

(51) Int. Cl.⁷ .......................... A61K 38/17; C07K 14/47
(52) U.S. Cl. .............................. 514/8; 514/21; 530/395
(58) Field of Search ........................... 514/2, 8, 12, 21; 530/350, 380, 386, 395, 412, 413, 416, 417, 420, 829, 830

(56) References Cited

U.S. PATENT DOCUMENTS

| | | | |
|---|---|---|---|
| 5,304,464 A | 4/1994 | Akerlöf et al. ................. | 514/8 |
| 5,453,354 A | 9/1995 | Akerlöf et al. ................. | 514/8 |
| 6,231,862 B1 * | 5/2001 | Majumder et al. ....... | 424/184.1 |
| 6,306,823 B1 * | 10/2001 | Majumder et al. ............. | 514/8 |

FOREIGN PATENT DOCUMENTS

| | | |
|---|---|---|
| WO | 90/12032 | 10/1990 |

OTHER PUBLICATIONS

Harris et al. Protein purification methods. Oxford:IRL Press. pp. 9,10,57–63, 1989.*

Harris et al. Protein purification methods: a practical approach, Oxford:IRL Press, pp. 40–51, 1989.*

Morita Z. and Chang M.C., "Maintenance of the Motility of Rat Epididymal Spermatozoa in the Presence of Male Accessory Secretions," Reprod. Fert., 24:247–254, 1971.

Hoskins D.D., Brandt H and Alcott T.S., "Initiation of sperm motility in the mammalian epididymis," Fed. Proc., 37:2534–2542, 1978.

Morton B.E., Fraser C.F. and Albagli L., Fertil. Steril., 32:99–106, 1979.

Brown D.V. and Senger P.L., "influence of Homologous Blood Serum on Motility and Head–to–Head Agglutination in Nonmotile Ejaculated Bovine Spermatozoa," Biol. Reprod., 23:271–275, 1980.

Mandal M., Banerjee S. and Majumdar G.C., "Stimulation of Forward Motility of Goat Cauda Epididymal Spermatozoa by a Serum Glycoprotein Factor," Biol. Reprod., 41:983–989, 1989.

Acott T.S. and Hoskins D.D., "Bovine Sperm Forward Motility Protein," J. Biol. Chem., 253:6744–6750, 1978.

Akerlöf et al., "Serum factors stimulate the motility of human spermatozoa," Int. J. Androl., 12:124–130, 1989.

Laemmli U.K., "Cleavage of Structural Proteins during the Assembly of the Head of Bacteriophage T4," Nature, 227:680–685, 1970.

* cited by examiner

*Primary Examiner*—Jeffrey E. Russel
(74) *Attorney, Agent, or Firm*—Caesar, Rivise, Bernstein, Cohen & Pokotilow, Ltd.

(57) ABSTRACT

The present invention relates to a new motility-promoting protein macromolecule and a process for the isolation of the motility promoting protein from buffalo serum/plasma, a slaughter house waste. The new motility promoting protein macromolecule preferably has a molecular mass of 66 kda. The process for preparation of a new motility-promoting protein from buffalo serum/plasma includes purifying the motility-promoting protein from the above fractionated serum/plasma by chromatography and electrophoresis methods.

17 Claims, No Drawings

PROCESS FOR THE PURIFICATION OF A NEW MOTILITY-PROMOTING PROTEIN FROM BUFFALO SERUM: A SLAUGHTER HOUSE WASTE

FIELD OF INVENTION

The present invention relates to a new motility-promoting protein macromolecule and a process for the isolation of the said motility promoting protein from buffalo serum/plasma: a slaughter house waste.

BACKGROUND OF THE INVENTION

Forward motility-promoting protein isolated from buffalo blood serum has the potential for the treatment of human infertility (due to low sperm motility) a great social curse in all human races. The product isolated by the present invention has also the potential for improving farm animal breeding with special reference to buffalo a milch animal of great economic importance in many countries including India.

Human infertility is a great social stigma in all human races as it brings personal miseries to the infertile people. It is generally believed that approx. 15% of the couples are infertile. A rough estimation shows that approx. 20 million Indian couples are infertile. It is thus evident that human infertility is a social problem of immense dimension all over the world. One of the main reasons of human male infertility is due to low order of sperm motility with normal cell count or normal sperm motility with lower sperm population in the ejaculated semen. Although several sophisticated Assisted Reproductive Technologies (e.g. IVF in vitro fertilisation, ICSI intracytoplasmic sperm injection) are available to solve the problems of oligospermic and asthenozoospermic patients ( with low sperm motility), these technologies are highly expensive and the success rate is extremely low. To solve the problem of human infertility due to low order of sperm motility, limited studies have been carried out for the isolation of motility promoting proteins from reproductive fluids and blood serum which are known to have sperm forward motility promoting potential(Morita Z. and Chang M. C. *J Reprod Fertil* 24, 247–254, 1971; Hoskins D. D., Brandt H and Acott T. S. *Fed Proc* 37, 2534–2542, 1978; Morton B. E., Fraser C. F and Albagli L.*Fertil Steril* 32, 99–106, 1979; Brown D. V. and Senger P. L. *Biol Reprod* 23, 271–275, 1980; Mandal M., Banerjee S. and Majumdar G. C. *Biol Reprod* 41, 983–989, 1989. Acott and Hoskins (Acott T. S. and Hoskins D. D. *J Biol Chem* 253, 6744–6750, 1978) have partially purified a 37 KDa glycoprotein from bovine seminal plasma/epididymal plasma which is essential for in vitro motility initiation in the immature bovine caput epididymal sperm. Akerlot et al (Akerlof E. Fredricsson B., Gustafson O., Lunell N. O. Nylund L., Rosenborg L., Slotte H and Pousette A., *Int J Androl* 12, 124–130, 1989) have demonstrated that human blood serum contains a protein (about 200 KDa) that activates forward motility of human ejaculated sperm. They have also made a patent on this human serum motility promoting protein (Akerlof, E. & Pousette, A., Patent No.WO 90 12 032, Oct. 18, 1990). The motility activating protein (approx. mol. Wt 200 KDa) has an isoelectric point of 5.1 and it comprises albumin, apolipoprotein designated as Al and immunoglobulin. The motility activating protein is usable for sperm motility assay and for the treatment of infertility. A pure protein complex of apolipoprotein and immunoglobulin of mol. wt. 180–250 KDa, has been isolated from human serum (U.S. Pat. No. 5,304,464, Apr. 19, 1994; U.S. Pat. No. 5,453,354, Sep. 26, 1995). The macromolecule also comprises albumin in equimolar amount with apolipoprotein Al and immunoglobulin. It has an isoelectric point of 5.1. The product stimulates sperm motility. Antibodies can be raised against this protein complex human infertility caused by sperm immotility can be treated by administering the product. It can be applied for both diagnostic and therapeutic uses. This product is rather expensive as it is derived from human blood serum.

OBJECT OF THE INVENTION

The main object of the present invention is to provide a new motility-promoting protein macromolecule having a molecular mass of 66 kda and a process for the isolation of said promoting protein from buffalo serum/plasma, a slaughter house waste which has potentiality for use in the treatment of human infertility (due to low sperm motility); a social problem of immense dimension in all countries. A major advantage of our isolated product (forward motility stimulating factor) is that as it is a product of slaughter house waste, it is economically more viable as a commercial product than the one from human serum developed earlier (patent Nos. WO 9012032, Oct. 18, 1990; U.S. Pat. No. 5,304,464, Apr. 19, 1994, U.S. Pat. No. 5,453,354, Sep., 26, 1995). No data are available on the motility promoting efficacy of the human serum product on spermatozoa of other species. The product of this invention can activate motility of sperm derived from various species including buffalo, bovine and goat. Another advantage of our product is that it has also the potential for improving the breeding of farm animals with special reference to buffalo; a milch animal of great economic importance in many countries.

DETAILED DESCRIPTION OF THE INVENTION

The present invention provides a new motility-promoting protein macromolecule and a process for the isolation of the said motility promoting protein from buffalo serum/plasma: a slaughter house waste, which comprises fractionating buffalo serum/plasma, purifying the motility promoting protein from the above fractionated serum/plasma by conventional chromatography and electrophoresis methods.

Further, the present investigation provides a new motility-promoting protein macromolecule and a process for the isolation of the said motility promoting protein from buffalo serum/plasma: a slaughter house waste. The invention comprises (a) purification and characterisation of a novel forward motility-stimulating protein from buffalo blood serum/plasma and (b) the methodologies for the purification of the motility-promoting protein from the buffalo serum/plasma. The motility-promoting factor is a heat stable protein. This invention reports for the first time the purification to apparent homogeneity of a motility-promoting protein from a biological fluid. It activates forward motility of ejaculated sperm of all the species tested (buffalo, bull goat rat hamster and human) indicating that there is no species specificity for its motility activating potential. The molecular mass of the motility promoter as estimated by sodium dodecyl sulphate polyacrylamide gel electrophoresis, high performance liquid chromatography and Sephadex G100 gel filtration is 66 KDa. The factor showed high protein specificity and affinity for activating sperm forward motility. The motility promoter at 0.5 $\mu$M level showed nearly maximal activity when 60–70% of spermatozoa were forward motility. It acts on the sperm cells with great rapidity to cause instant activation of sperm motility. It is a glycoprotein that binds with high affinity to concanavalin A. It is an acidic protein with isoelectric point of 3.7 (approx.) and its activity is dependent on $Mg^{++}$. Motility promoting protein has markedly higher efficacy for activating sperm motility than theophylline or bicarbonate or their combination. The sperm motility induced by the factor is greatly stabilized by bicarbonate. Amino acid analysis shows that it is rich in aspartic acid, glutamic acid and leucine. Both the sugar and protein parts of the molecule are essential for its biological activity. Specific receptors of motility promoting protein have been demonstrated on the sperm surface that may mediate the action of the factor on sperm. It is strongly immunogenic. Studies with antisera against the buffalo motility promoting protein (raised in rabbit) show that the antisera cross react with sera derived from goat, bull, cow and human. The data implicate that the motility promoter or motility promoter like proteins are present in the sera of other species. Using the antibody against the motility stimulating factor, the motility promoter has been shown to be present in testis and epididymis although liver is the richest source of it. The product isolated by the present invention is a new motility promoting protein as its characteristics are clearly different from those reported in the literature.

A part of the invention consists of development of the methodologies for the isolation of motility promoting protein from buffalo blood, a slaughter house waste. Motility promoting protein activity is also present in the blood sera of all the species tested including human but buffalo blood is the richest source of this factor(Mandal M., Banerjee S. and Majumder G. C. Biol Reprod 41, 983–989, 1989). The factor can be isolated from blood serum or plasma. Blood serum/plasma was first fractioned with ammonium sulphate. The motility promoter was sedimented with 40–80% saturation of the salt. The salt fraction of motility promoting protein was then subjected to a cation exchange chromatography using a resin such as carboxymethyl cellulose/Sephadex using low ionic acidic buffer (e.g. 10 mM Sodium acetate, pH 5.6). The factor binds to the resin and it can be eluted from the column at higher concentrations of salt such as 0.4 M NaCl. The motility promoting protein can also be purified by anion exchange chromatography using diethylaminoethyl cellulose/Sephadex as the resin and low ionic alkaline buffer (e.g. 10 mM Tris-HCl, pH 8.3) when the motility promoter does not bind to the resin. The partially purified motility promoting protein as obtained after ion exchange chromatography was purified further by molecular sieving chromatography using Sephadex as the insoluble matrix or high performance liquid chromatography column using phosphate buffer of varying pH (6.9 to 7.5) and varying ionic strength (50–100 mM).The motility promoter can as well be purified by adsorption chromatography using insoluble gel matrix (e.g alumina gel). The factor binds to the gel and can be eluted at a relatively high concentration of salt (e.g 1 M Tris HCl, pH 7.4). Chromatofocusing utilising polybuffer exchanger termed as PBE 94 resin (Pharmacia) can as well be used for the purification of motility promoting protein. Motility promoting protein binds to the concanavalin A-Agarose affinity matrix and it can be eluted from the column with α-methyl-D-mannoside. A suitable combination of these procedures lead to approx. 100 to 400 fold purification of the motility promoter from serum/plasma with recovery of approx. 20 to 30%. The partially purified factor can be purified to apparent homogeneity by using native polyacrylamide gel electrophoresis under a variety of electrophoretic conditions including different percentages (7 to 10%) of the polyacrylamide gel. The resulting pure motility promoting protein was approx. 600 fold purified and the recovery of the activity was approx. 20%. Nearly 3 to 4 mg of pure motility promoting protein was obtained per 100 ml of the blood serum/plasma.

This invention is also relating to pharmaceutical preparations comprising a macromolecule of proteinaceous nature which is essentially pure, has a molecular weight of about 66 KDa and activates sperm motility together with any suitable excipient. Examples of suitable excipients are culture media or other salt solutions. The pharmaceutical preparations are prepared according to methods known per se. The pharmaceutical preparations according to the invention have potentiality for the treatment of infertility.

The invention pertaining to the methodology of the isolation of serum motility promoter is further being illustrated below with two examples and should not be construed to limit the scope of the present invention.

Example 1

Buffalo blood samples were collected from a local slaughter house and then allowed to clot at 5° C. overnight. Serum was obtained by centrifugation of the clotted blood at 14,000 g for 15 min. The serum contained approx. 180 units of motility promoting protein activity/ml of serum, one unit of motility promoting protein activity being defined as the amount of the factor that induces forward motility in 10% of the cells.

Two hundred ml of blood serum (approx. 100 mg protein/ml) was subjected to ammonium sulphate fractionation by using 0–40%, 40–60% and 60–80% saturation of ammonium sulphate. In each step the protein suspension was centrifuged for 15 min at 18000×g and the sedimented protein pellet was dissolved in 10 mM Tris HCl, pH 8.3 while the supernatants were subjected to further saturation by the addition of the solid salt. The fractions were then dialysed extensively in a cold room (4°C.) against a modified Ringer's solution termed as RPS medium pH 6.9 (119 mM NaCl—5 mm KCl—1.2 mM MgSO4—10 mM glucose penicillin (50 units/ml)—16.3 potassium phosphate buffer pH 6.9). Approx. 90% of the motility promoting protein activity was sedimented by 60–80% saturation of ammonium sulphate. The active fraction from $(NH_4)_2 SO_4$ fractionation was purified further by ion-exchange chromatography in a column (1×30 cm) of carboxymethyl-cellulose previously equilibrated with 10 mM sodium acetate buffer pH 5.6. After passage of the sample, the column was washed with 30 ml of 10 mM sodium acetate buffer, pH 5.6. The column was then eluted successively with 30 ml each of 10 mM sodium acetate buffer, pH 5.6 with NaCl having concentrations of 0.2 M, 0.4 M, 0.6 M and 1 M. Motility promoting protein binds to the resin and the major amount of motility promoting protein activity was eluted with 10 mM sodium acetate—0.2 M NaCl buffer, pH 5.6. The motility promoting protein preparation was then concentrated with polyethyleneglycol compound and dialysed extensively in a cold room against 0.1 M potassium phosphate buffer, pH 6.9. By these procedures motility promoting protein was purified to about 100—fold.

Motility promoting protein was then subjected to High Performance Liquid Chromatography. The concentrated motility promoting protein preparation was chromatographed on a high performance liquid chromatography gel filtration column termed as LKB Ultrofac, TSK 3000 SWG (21.5×600 mm) with constant monitoring of absorbance at 280 nm in a spectrophotometer (481 LC, Waters) equipped with a 475B data module (Waters). Mobile phase used was 0.1 M potassium phosphate buffer, pH 6.9 at a flow rate of 2.2 ml/min. High performance liquid chromatography was carried at room temperature and the active fractions were collected in an iced container. Retention time of motility promoting protein was 43.5 minutes and it was the major peak which represented approx. 60% of serum motility promoting protein activity. Motility promoting protein was purified further by using 7.5% native polyacrylamide tube gel electrophoresis according to Laemmli (Laemmli U. K Nature, 227, 680–685, 1970). Before sample application, the gel was pre-run for 15 minutes. After electrophoresis one gel was stained with Coomassie Blue for the detection of protein bands and another gel was sectioned to slices, the thickness of each gel slice being 0.5 cm. For the elution of motility promoting protein activity each gel slice was dispersed in 0.5 ml of RPS medium, pH 7.35 overnight at 4° C. After staining the gel showed two major protein bands of Rf values 0.3 and 0.6 respectively and from activity measurement it was observed that protein band of Rf value 0.6 showed major motility promoting protein activity. For preparative work, several numbers of tube gels were run and protein band of Rf value 0.6 was eluted from each gel. The pooled fraction was then concentrated by filtration through Amicon PM-10 membrane and was stored at −70° C. Unless otherwise specified all the purification steps were conducted at 0–4° C. By these procedures motility promoting protein was purified to apparent homogeneity (about 600—fold purified), the specific activity of the isolated purified factor being about 1100 units/mg protein. The yield of pure motility promoting protein was approx. 7 mg from 200 ml of serum and the overall recovery of its activity was about 20%.

Example 2

Buffalo blood from slaughter house was collected in a conical flask containing sodium citrate (2.6%) to prevent clotting of blood. Blood plasma was then separated from blood cells by centrifugation at 6500×g for 5 min. The blood plasma (400 ml) was then fractionated by using ammonium sulphate as described in "Example 1". The active motility promoting protein fraction was first dialysed against 10 mM Tris-HCl , pH 8.3 and then subjected to diethylaminoethyl cellulose chromatography. The resin was equilibrated with 10 mM Tris HCl, pH 8.3. After passage of the sample (50 ml) the column (30×1.5 cm) was washed with 80 ml of the equilibrating buffer. The column was then eluted successively with 80 ml each of Tris-HCl, pH 8.3 having concentrations of 0.1 M, 0.2 M, 0.3 M, 0.5 M and 1 M Tris HCl. Before activity measurement, each fraction was dialysed against 10 mM Tris HCl, pH 7.4. Major portion of motility promoting protein activity (approx. 85%) did not bind to the resin. The unretained fraction of diethylaminoethyl cellulose chromatography was concentrated by polyethyleneglycol compound and then dialysed against 10 mm Sodium acetate buffer, pH 5.6. The dialysed motility promoting protein fraction was subjected to ion-exchange chromatography on a column (30×1 cm) of carboxymethyl cellulose previously equilibrated with 10 mM sodium acetate, pH 5.6. After passage of the sample (10 ml) the column was washed with 30 ml of 10 mM sodium acetate buffer, pH 5.6. The column was then eluted successfully with 30 ml. each of 10 mM Sodium acetate buffer pH 5.6 with NaCl having concentrations of 0.1 M, 0.2 M, 0.5 M and finally with 10 mM sodium acetate buffer, pH 5.6 containing 1 M NaCl. The major amount of motility promoting protein activity was eluted with 10 mM sodium acetate, pH 5.6 containing 1 M NaCl. The resulting motility promoting protein activity was mixed with 10 ml of alumina gel (50 mg/ml, Sigma Chemical Co.) suspended in 10 mM Tris HCl, pH 7.4. Thee mixture was stirred for 45 min in ice. The suspension was then centrifuged at 500×g for 10 min. The supernatant (unadsorbed fraction) was rejected and the motility promoting protein was eluted from the pellet with 1 M Tris—HCl, pH 7.4. The preparation of motility promoting protein was concentrated with polyethyleneglycol compound and finally dialysed extensively against 25 mM ethanolamine—HCl, pH 9.4. The motility promoting protein was further purified by chromatofocusing on polybuffer exchanger termed as PBE 94:a Pharmacia Product. A column (15×1 cm) of ion exchange resin polybuffer exchanger termed as PBE-94 was equilibrated with the above buffer and the motility promoting protein sample was applied to it. After the sample passed through, the column was washed with the equilibrating buffer. Motility promoting protein was eluted with poly buffer 96-HCl, pH 7.0 (Pharmacia) and the volume in each fraction was 4.5 ml. The active fractions were pooled, concentrated by polyethyleneglycol compound and finally dialysed against 10 mM potassium phosphate buffer containing 0.154 M NaCl. All the purification steps were carried out at 0–4° C. The factor was purified to approx. 400—fold with approx. 25% recovery. The isolated motility promoting protein was approx. 70% pure. About 14 mg of the partially purified motility promoting protein was obtained from 400 ml of blood plasma.

TABLE

Amino acid composition of PMST.

| Amino Acid | Mole percent |
|---|---|
| Aspartic acid + Asparginine | 10.38 |
| Glutamic acid + Glutamine | 9.13 |
| Serine | 8.21 |
| Glycine | 8.51 |
| Histidine | 4.23 |
| Arginine | 5.04 |
| Threonine | 4.88 |
| Alanine | 6.59 |
| Proline | 6.05 |
| Tyrosine | 3.61 |
| Valine | 4.64 |
| Methionine | 1.33 |
| Cystine | 1.09 |
| Isoleucine | 3.01 |
| Leucine | 11.21 |
| Phenylalanine | 5.18 |
| Lysine | 6.89 |

We claim:

1. An isolated sperm motility-promoting glycoprotein macromolecule having a molecular mass of 66 kda and purified to homogeneity.

2. The isolated sperm motility-promoting glycoprotein macromolecule as claimed in claim 1, comprising about 10 mole percent aspartic acid and asparagine, about 9 mole percent glutamic acid and glutamine and about 11 mole percent leucine.

3. The isolated sperm motility-promoting glycoprotein macromolecule as claimed in claim 1, comprising about 10 mole percent aspartic acid and asparagine residues.

4. The isolated sperm motility-promoting glycoprotein macromolecule as claimed in claim 1, comprising about 9 mole percent glutamic acid and glutamine residues.

5. The isolated sperm motility-promoting glycoprotein macromolecule as claimed in claim 1, comprising about 11 mole percent leucine residues.

6. The isolated sperm motility-promoting glycoprotein macromolecule as claimed in claim 1, having an isoelectric point of 3.7.

7. The isolated sperm motility-promoting glycoprotein macromolecule as claimed in claim 1, which is $Mg^{2+}$ dependent.

8. The isolated sperm motility-promoting glycoprotein macromolecule as claimed in claim 1, which has a 60% heat stability at 100° C. for 5 min.

9. The isolated sperm motility-promoting glycoprotein macromolecule as claimed in claim 1, comprising a sugar side chain essential for sperm motility promotion.

10. The isolated sperm motility-promoting glycoprotein macromolecule as claimed in claim 1, which stimulates forward motility of sperm derived from buffalo, human, bull, goat, ram, rat and hamster.

11. The isolated sperm motility-promoting glycoprotein macromolecule as claimed in claim 1, wherein an antibody raised against said sperm motility-promoting glycoprotein macromolecule cross-reacts with goat, bull, cow and human blood sera.

12. A process for the preparation of the isolated sperm motility-promoting glycoprotein macromolecule of claim 1, said process comprising:

fractionating at least one of buffalo serum and buffalo plasma to provide a fractionated preparation; and purifying the sperm motility-promoting glycoprotein from the fractionated preparation by chromatography and electrophoresis.

13. A process as claimed in claim 12, wherein fractionation is effected using ammonium sulphate in a concentration range up to 80% (w/v) saturation.

14. A process as claimed in claim 12, wherein the purification of protein is effected by ion-exchange chromatography, molecular sieving chromatography, chromatofocussing and high performance liquid chromatography.

15. A process as claimed in claim 12, wherein an ion-exchange resin used in the chromatography is selected from the group consisting of carboxymethyl-cellulose diethylaminoethyl-cellulose, and PBE 94 polybuffer exchange resin.

16. A process as claimed in claim 12, wherein an eluent used in the chromatography is a phosphate buffer having a pH ranging between 6.9 to 7.5 in varying ionic strength in a range of 50–100 mM.

17. A method for enhancing sperm motility in-vitro comprising adding a pharmaceutical composition to sperm in-vitro, wherein said pharmaceutical composition comprises:

the isolated sperm motility-promoting glycoprotein macromolecule of claim 1, and a pharmaceutically acceptable excipient, to thereby enhance sperm motility.

* * * * *